US009792798B2

(12) United States Patent
Jobin et al.

(10) Patent No.: US 9,792,798 B2
(45) Date of Patent: *Oct. 17, 2017

(54) CONTEXT-AWARE WEARABLE SAFETY SYSTEM

(71) Applicant: General Electric Company, Schenectady, NY (US)

(72) Inventors: James Jobin, San Ramon, CA (US); Roberto Silveira Silva Filho, Dublin, CA (US); Bo Yu, San Ramon, CA (US)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/407,187

(22) Filed: Jan. 16, 2017

(65) Prior Publication Data

US 2017/0124832 A1   May 4, 2017

Related U.S. Application Data

(63) Continuation of application No. 14/686,573, filed on Apr. 14, 2015, now Pat. No. 9,547,970.

(51) Int. Cl.
  *G08B 21/02*   (2006.01)
  *H04B 5/00*   (2006.01)
  (Continued)

(52) U.S. Cl.
  CPC ......... *G08B 21/02* (2013.01); *G08B 21/0453* (2013.01); *H04B 1/385* (2013.01); *H04B 5/0062* (2013.01); *H04B 2001/3866* (2013.01)

(58) Field of Classification Search
  CPC .. G08B 21/043; G08B 21/0476; G08B 25/08; G08B 21/04; G08B 21/02;
  (Continued)

(56) References Cited

U.S. PATENT DOCUMENTS 9,547,970 B2   1/2017   Jobin et al.
2011/0291827 A1   12/2011   Baldocchi et al.
(Continued)

FOREIGN PATENT DOCUMENTS

WO   WO-2016168498 A3   10/2016

OTHER PUBLICATIONS

U.S. Appl. No. 14/686,573, Examiner Interview Summary dated Aug. 12, 2016, 3 pgs.
(Continued)

*Primary Examiner* — Ted Wang
(74) *Attorney, Agent, or Firm* — Schwegman Lundberg & Woessner, P.A.

(57) ABSTRACT

In an example embodiment, biometric data and environmental data are obtained from sensors. Corporate information system (CIS) information is retrieved for a worker, with the CIS information including a schedule of tasks assigned to the worker. A task currently being performed by the worker is determined based on the schedule of tasks. Weights are assigned to the biometric data and the environmental data. The weights vary between data from different sensors, with the weights assigned based on the task currently being performed by the worker. A current safety score is assigned for the worker based on the calculation of a formula, with the formula using the assigned weights as coefficients to variables, with the variables being values obtained from the biometric data and the environmental data. The current safety score is compared to a safety threshold, and if the threshold is violated, an alert is generated to the worker.

20 Claims, 8 Drawing Sheets

(51) Int. Cl.
*H04B 1/3827* (2015.01)
*G08B 21/04* (2006.01)

(58) Field of Classification Search
CPC .. G08B 21/0453; H04B 5/0062; H04B 1/385; H04B 2001/3866
See application file for complete search history.

(56) References Cited

U.S. PATENT DOCUMENTS

| | | |
|---|---|---|
| 2012/0139721 A1 | 6/2012 | Betts et al. |
| 2014/0058680 A1 | 2/2014 | Geva et al. |
| 2016/0048298 A1* | 2/2016 | Choi ................... G06F 3/04842 715/846 |
| 2016/0307425 A1 | 10/2016 | Jobin et al. |

OTHER PUBLICATIONS

U.S. Appl. No. 14/686,573, Non Final Office Action dated Apr. 20, 2016, 9 pgs.
U.S. Appl. No. 14/686,573, Notice of Allowance dated Sep. 8, 2016, 10 pgs,.
U.S. Appl. No. 14/686,573, Response dated Aug. 22, 2016 to Non Final Office Action dated Apr. 20, 2016, 9 pgs.
International Application Serial No. PCT/US2016/027588, International Search Report dated Sep. 30, 2016, 3 pgs.
International Application Serial No. PCT/US2016/027588, Written Opinion dated Sep. 30, 2016, 3 pgs.

\* cited by examiner

|  | Temp. 402A | Heart Rate 402B | Glucose 402C | Radiation Level 402D |
|---|---|---|---|---|
| Strenuousness = "easy" 404A | 1.1 | 1.5 | 1.04 | |
| Strenuousness = "mostly easy" 404B | 1.05 | 1.25 | 1.02 | |
| Strenuousness = "moderate" 404C | 1 | 1 | 1 | |
| Strenuousness = "somewhat strenuous" 404D | 0.95 | 0.75 | 0.98 | |
| Strenuousness = "strenuous" 404E | 0.9 | 0.5 | 0.96 | |
| Dangerousness = "completely safe" 404F | 1.1 | 1.5 | | 3 |
| Dangerousness = "somewhat safe" 404G | 1.05 | 1.25 | | 2 |
| Dangerousness = "moderately safe" 404H | 1 | 1 | | 1 |
| Dangerousness = "somewhat dangerous" 404I | 0.95 | 0.75 | | 0.9 |
| Dangerousness = "extremely dangerous" 404J | 0.9 | 0.5 | | 0.8 |

*FIGURE 4*

CONTEXT-AWARE WEARABLE SAFETY SYSTEM

CLAIM OF PRIORITY

This application is a continuation of and claims the benefit of priority under 35 U.S.C. §120 to U.S. patent application Ser. No. 14/686,573, filed on Apr. 14, 2015, which is hereby incorporated by reference herein in its entirety.

TECHNICAL FIELD

This application relates generally to safety systems for workers. More particularly, this application relates to a context-aware wearable safety system.

BACKGROUND

The safety of a field engineer in an industrial environment is of upmost concern to an employer. Many of the duties undertaken by field engineers can be dangerous. Safety-related costs, both for preventative measures and dealing with safety incidents, can easily cost a company millions of dollars annually. Safety equipment, despite recent advances, is still very low-tech. Current approaches include mandatory use of safety equipment, the buddy system (where workers perform tasks in pairs), periodic check pointing (where workers communicate with a command and control center reporting status), body sensors, and use of remote monitoring technology such as closed circuit television. While accuracy of various body sensors have been improved, this safety equipment lacks the ability to judge context. Many body parameters may change and fluctuate in normal situations. For example, a heart rate monitor may be able to determine whether a worker's heart rate is exceeding a particular threshold, but there is no regard for whether this threshold is proper given the current context. For example, a heart rate of 150 beats per minute (bpm) may be perfectly acceptable if the worker is currently performing a physically intensive task, such as lifting a heavy object, but may not be acceptable if the worker is currently sitting watching someone else lift a heavy object. Because the thresholds used in traditional sensors are often wildly inaccurate for the present context, there is a tendency to ignore alerts issued based on those thresholds, and once a worker begins to ignore alerts, there is an increased tendency for the worker to ignore an alert that is truly necessary.

BRIEF DESCRIPTION OF DRAWINGS

The present disclosure is illustrated by way of example and not limitation in the figures of the accompanying drawings, in which like references indicate similar elements and in which:

FIG. 4 is an example of a table assigning weights to various combinations of task categories and sensor input types, in accordance with an example embodiment.

DETAILED DESCRIPTION

Overview

Figure 1:
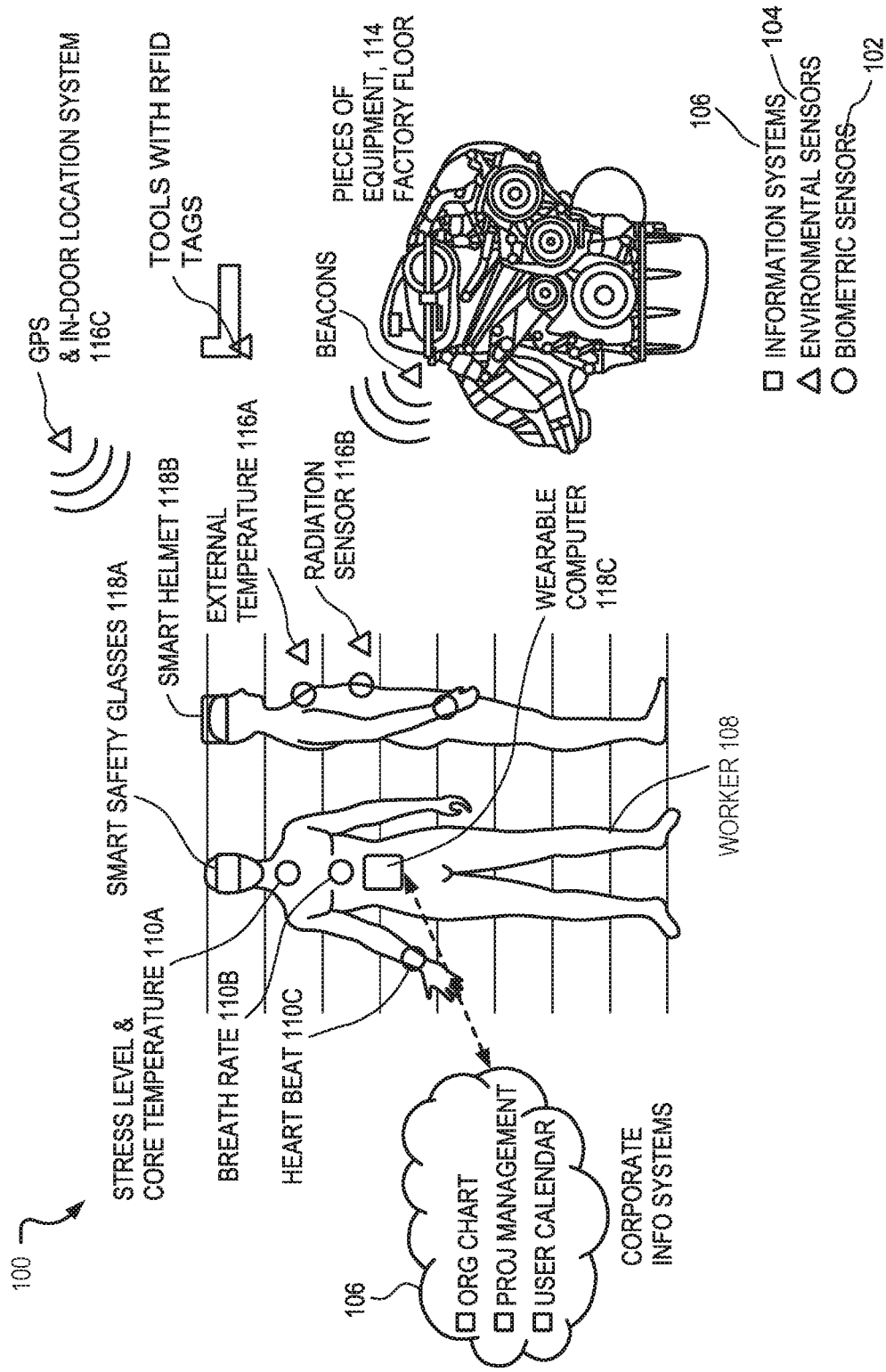
FIG. 1 is a diagram illustrating a system, in accordance with an example embodiment, for context-aware safety monitoring.

The description that follows includes illustrative systems, methods, techniques, instruction sequences, and machine-readable media (e.g., computing machine program products) that embody illustrative embodiments. In the following description, for purposes of explanation, numerous specific details are set forth in order to provide an understanding of various embodiments of the inventive subject matter. It will be evident, however, to those skilled in the art that embodiments of the inventive subject matter may be practiced without these specific details. In general, well-known instruction instances, protocols, structures, and techniques have not been shown in detail.

In an example embodiment, an integrated system is provided combining body sensing and environmental sensing with corporate information systems in support of safety for workers in industrial settings. Recognizing that information from different sources, when combined, can increase accuracy and better infer the user's status, information from multiple sensors, including both body sensors and environmental sensors, can be combined to make certain assumptions. For example, if the outside temperature is high (as detected by an environmental sensor), a worker's heart rate (as detected by a body sensor) may be higher than under ordinary circumstances. Hence, a threshold related to heart rate may be raised when the outside temperature is high. Additionally, both body sensor and environmental sensor data can be combined with corporate information system data to further improve the adjustment of thresholds. For example, a particular user may be assigned various tasks for the day, some of which are physically intensive and some of which are not. Thus, for example, if the worker is currently performing a physically intensive task (as per a current task assigned to the worker in the corporate information system), the heart rate threshold may be raised.

Body sensor data refers to any data derived from one or more body sensors monitoring a particular worker. Body sensors may monitor any bodily function or parameter of the individual worker. Examples include, but are not limited to, heart rate sensors, temperature sensors, respiration sensors, blood pressure sensors, glucose level sensors, microphones/voice analysis sensors, sweat sensors, electrocardiogram (ECG) sensors, electromyography (EMG) sensors, pulse oxide sensors, location sensors, and weight sensors.

Environmental sensor data refers to any data derived from one or more environmental sensors monitoring a particular area. Environmental sensors may monitor any aspect of the area, including temperature, humidity, noise levels, light levels, radiation levels, ultraviolet rays, and gas levels.

Corporate information system data refers to any data derived from a corporate information system. Examples include, but are not limited to, worker task schedules/ calendars, work location and information about the location, employee health records, and management hierarchy (who to contact if threshold is exceeded).

In an example embodiment, the body sensor data, environmental sensor data, and corporate information system data can be continuously monitored and examined with probability and confidence interval values. This information can then be blended with the aid of a rules engine. Alerts can then be generated and safety information can be sent to the proper personnel.

FIG. 1 is a diagram illustrating a system 100, in accordance with an example embodiment, for context-aware safety monitoring. As described briefly earlier, the system 100 integrates data from three sources: body sensors 102, environmental sensors 104, and corporate information system 106. Body sensors 102 may be worn by or otherwise affixed to a worker 108. The body sensors 102 depicted here include a stress level and core temperature sensor 110A, a breath rate sensor 110B, and a heart beat sensor 110C. Environmental sensors 104 may be affixed to aspects of the environment, such as factory walls or a piece of factory equipment 114, or may alternatively be worn by or otherwise affixed to the worker 108. The environmental sensors 104 depicted here include external temperature sensor 116A, radiation sensor 116B, Global Positioning System (GPS) sensor 116C, and Radio Frequency identification (RFID) sensors. The worker 108 may, for example, scan a badge having an RFID chip in it using the RFID sensor affixed to the piece of factory equipment 114 to indicate that the worker has begun to work on the piece of factory equipment 114. Alternatively, one or more tools used by the worker 108 may contain an RFID chip to indicate that the worker is using a particular tool. This information may be used to, for example, deduce that the worker 108 is located at a particular location in the factory or that the worker 108 is currently performing a particular task on his or her schedule.

Also depicted are various items that can be used to display alerts or other information to the worker 108. This includes smart safety glasses 118A, a smart helmet 118B, and a wearable computer 118C. The smart safety glasses 118A may include a small projector able to project information on the lens of the smart safety glasses 118A to notify the user of various information. The smart helmet 118B may include a speaker or headphones to audibly inform the user of various information. The wearable computer 118C may include a display that is visible to the user when he or she looks down and upon which may be displayed an organization chart, project management information, and a user calendar, as well as any relevant alerts.

Also depicted is a corporate information system 106, which may include a hardware server upon which personal and project task management information as well as organization data may be stored. As will be described in more detail below, a rules engine may then monitor the data from the body sensors 102, environmental sensors 104, and corporate information system 106. In one example embodiment, the rules engine is located on the same hardware server as the corporate information system 106, but in other embodiments the rules engine is located on a separate hardware server.

Figure 2:
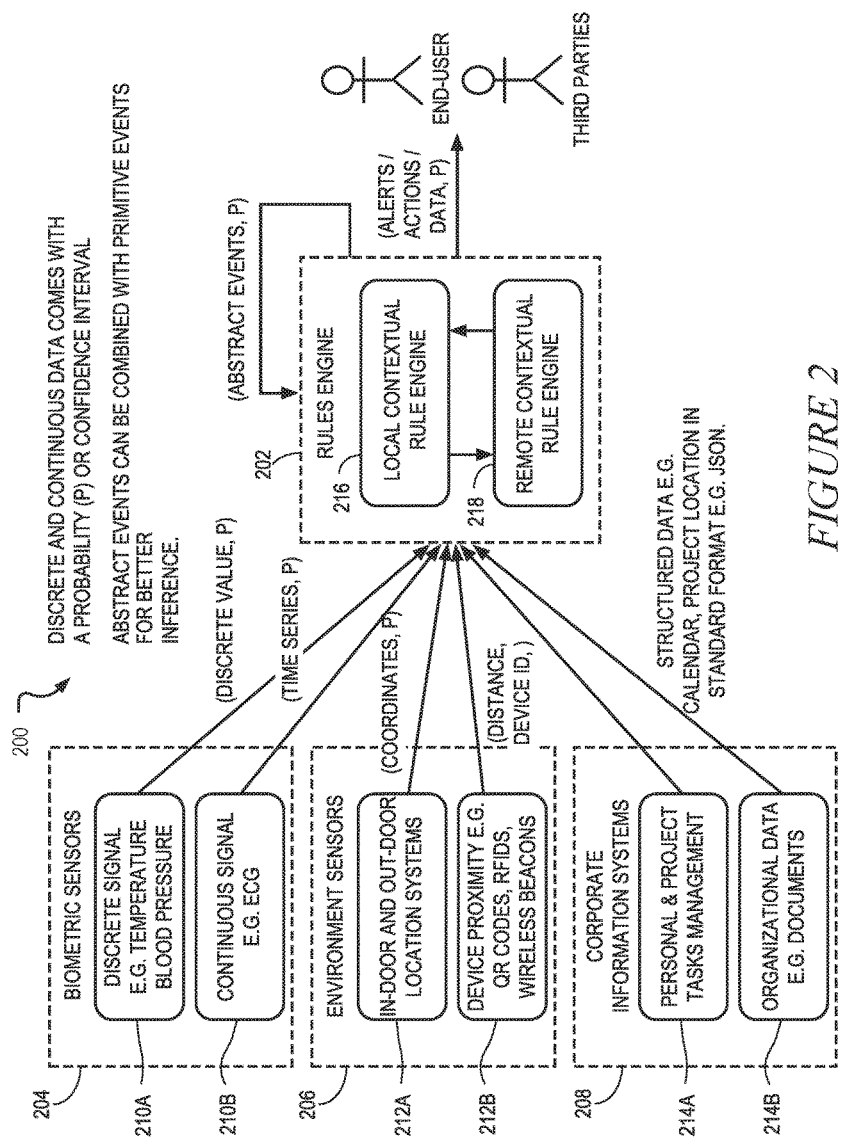
FIG. 2 is a logical diagram illustrating a system, in accordance with an example embodiment, for context-aware safety monitoring.

FIG. 2 is a logical diagram illustrating a system 200, in accordance with an example embodiment, for context-aware safety monitoring. A rules engine 202 may receive various pieces of data from body sensors 204, environmental sensors 206, and corporate information systems 208. Referring first to the body sensors 204, the data received from the body sensors 204 may include discrete signals 210A such as temperature and blood pressure (in which case the signals include discrete values) and/or continuous signals 210B such as ECG information (in which case the signals include time series values).

Referring to the environmental sensors 206, the data received from the environmental sensors 206 may include coordinate information 212A such as from location sensors and/or discrete signals such as temperature, humidity, or proximity information (such as RFID scans or wireless beacons) as well as device proximity information 212B, such as scanned QR codes, scanned RFIDs, wireless beacons and the like.

Referring to the corporate information systems 208, the data received from the corporate information systems 208 may include personal and project tasks management data 214A and/or organizational data 214B.

The rules engine 202 may include a local contextual rule engine 216 and a remote contextual rule engine 218. In an example embodiment, the local contextual rule engine 216 and remote contextual rule engine 218 are located on different components but work in conjunction with one another. The local contextual rule engine 216 may focus on the body sensors 204 and be located locally on the worker's person or thereabouts. The remote contextual rule engine 218 focuses on filtering data from corporate services, defining triggers to information changes, and notifying the client context engine. This allows a certain degree of privacy for the data from the body sensors 204. The local contextual rule engine 216 can obtain the data from the environmental sensors 206 and corporate information systems 208 from the remote contextual rule engine 218 to perform its functions (although in some embodiments the data from the environmental sensors 206 is obtained directly from the environmental sensors 206 or another component). Information from the remote contextual rule engine 218 may be fetched periodically by the local contextual rule engine 216 for enriching the local context (e.g., knowledge about the current user assignments, tasks, etc.). The remote contextual rule engine 218 can generate notifications of new user assignments, new tasks, new meetings, and the like, and the local contextual rule engine 216 can then use these notifications to update a local cache and combine that information with data from the various body sensors 204 and environmental sensors 206, thus merging corporate information with sensor data into the user context.

When the local contextual rule engine 216 cannot connect to the remote contextual rule engine 218, a local cache of the remote context can be used. When connection is reestablished, data between the local contextual rule engine 216 and the remote contextual rule engine 218 can be synchronized, causing pending notifications to be sent to the user and context subscriptions to be updated.

Thus, the local contextual rule engine 216 and the remote contextual rule engine 218 work together to integrate data, including continuous and discrete signals, from physical and logical sources and provide probabilistic determination of whether a certain condition is a safety hazard.

Information from body sensors 204 and environmental sensors 206 can be considered as a way to mitigate the effects of false positives, utilizing their accuracy and confidence intervals, as well as information probability. For example, temperature sensors may have accuracy measures in +−0.5 degrees, a motion sensor may detect correct user movements 90% of the time, and an environmental sensor can detect UV radiation levels with 80% accuracy. All of this information may be considered when assigning weights to the various pieces of data as part of a deterministic algorithm to determine whether a safety issue exists in the current context.

In an example embodiment, machine learning algorithms can be used to integrate and analyze all of the input data in real time and provide finer tuned probabilities of potential issues.

Figure 3:
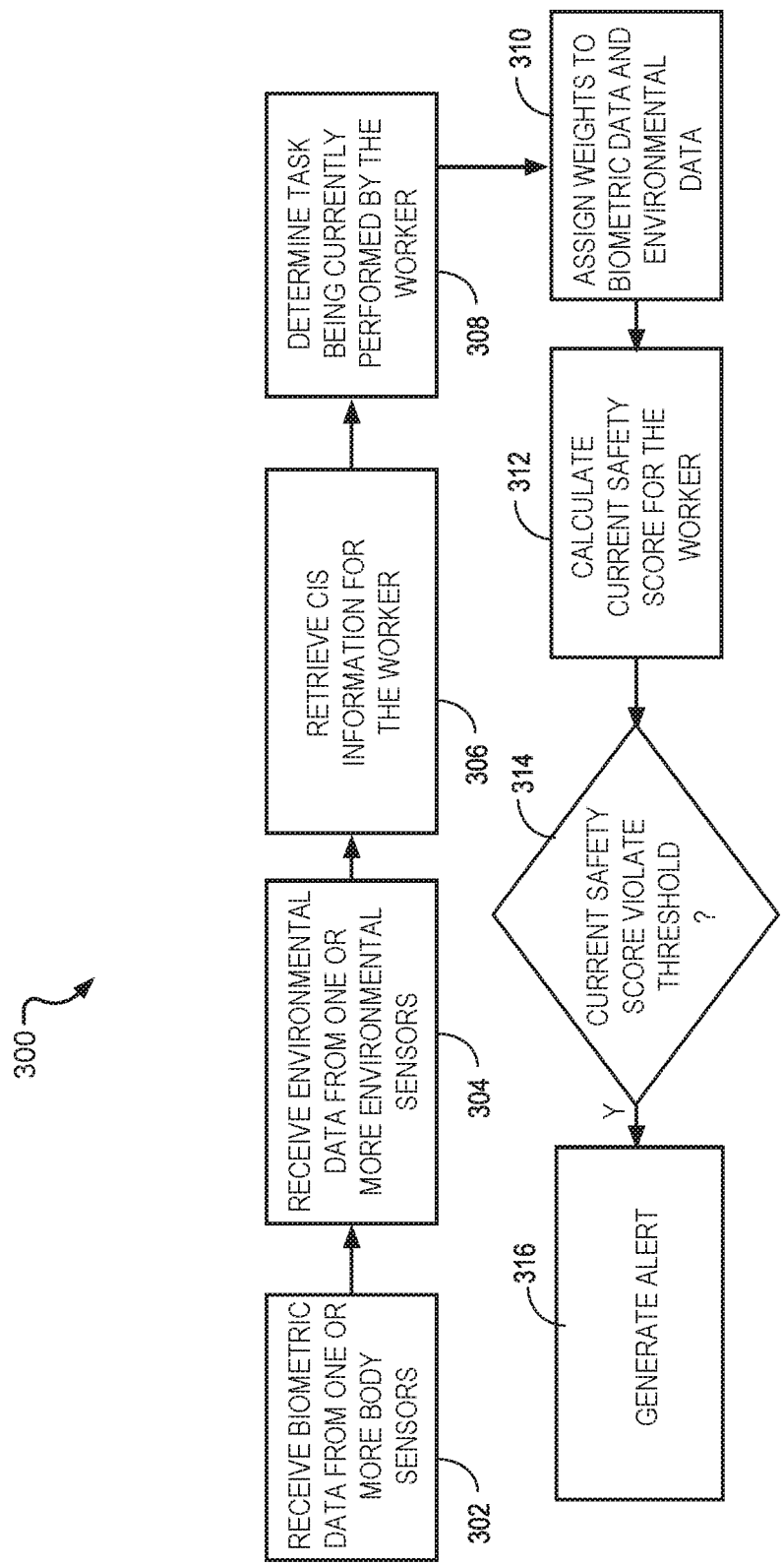
FIG. 3 is a flow diagram illustrating a method, in accordance with an example embodiment, of generating safety alerts.

FIG. 3 is a flow diagram illustrating a method 300, in accordance with an example embodiment, of generating safety alerts. At operation 302, biometric data is received from one or more body sensors monitoring a worker. At operation 304, environmental data is received from one or more environmental sensors in an area surrounding the worker. At operation 306, Corporate information System (CIS) information is retrieved for the worker. The CIS information can include a schedule of tasks assigned to the worker.

At operation 308, a task currently being performed by the worker can be determined. This may be determined by using, for example, the schedule of tasks assigned to the worker and comparing it to various input information, such as the current time, data input by the worker (e.g., checked off completed tasks), RFID scans, and the like, or any other information that can be used to determine which particular task the worker is currently performing.

At operation 310, weights may be assigned to the biometric and environmental data, with the weights varying based on the task currently being performed by the worker. Thus, for example, a particular weight may be assigned to data from a heart rate sensor if the worker is performing a strenuous task while a different weight may be assigned to the data from the heart rate sensor if the worker is not performing a strenuous task. The determination may be accomplished in a number of different ways. In an example embodiment, the current task being performed may be assigned into one or more categories of tasks. Each category of task may be associated with different weights for different sensors. It should be noted that it is not necessary that merely one category be assigned to a particular task. In some example embodiments, multiple categories may be assigned to particular task. For example, one category type may relate to how physically strenuous the task is (perhaps being assigned as one of five categories for the category type ("easy," "mostly easy," "moderate," "somewhat strenuous," and "strenuous"). Thus, a physically grueling task, such as lifting an extremely heavy object and moving it across a room, may be assigned as "strenuous" whereas a non-physically grueling task, such as sitting on a stool and unscrewing a panel, may be assigned as "easy." Another category type may relate to the inherent dangerousness of the task (perhaps being assigned as one of five categories for the category type ("completely safe," "somewhat safe," "moderately safe," "somewhat dangerous," and "extremely dangerous"). Thus, a very dangerous task, such as servicing the inside of a nuclear reactor or handling a high-power wire, may be assigned as "extremely dangerous."

A table showing weights to be assigned to sensor data may be maintained. This table may include a weight assignment for each of multiple combinations of task category and sensor. It should be noted that it is not necessary for this table to maintain weights for all possible combinations, and indeed it may very well be that data from certain sensors should not be affected by a particular task category type. This may be based on a lack of correlation between the underlying event or condition being monitored by the sensor and the particular task category. For example, a radiation level may not be at all related to the strenuousness of an activity, and thus in an example embodiment where strenuousness of a task is a task category type in the table and a radiation sensor is the sensor in the table, there may simply be no weight assigned to such a combination, regardless of the task category (e.g., "easy") assigned to the strenuousness of the individual task.

FIG. 4 is an example of a table 400 assigning weights to various combinations of task categories and sensor input types, in accordance with an example embodiment. The table 400 assigns temperature input (e.g., from a thermometer) in one column 402A, heart rate input (e.g., from a pulse meter) in a second column 402B, glucose level (e.g., from a glucose meter) in a third column 402C, and radiation level (e.g., from a Geiger counter) in a fourth column 402D. Here there are two task category types that a current task can be assigned to; strenuousness and dangerousness. The table 400 assigns the various task categories as rows 404A-404J. As can be seen, many of the combinations of task categories and sensor input types (such as, for example, the combination of a strenuous task 404E and temperature 402A resulting in weight 406) include weights for the combinations. Some of the combinations of task categories and sensor input types, however, contain no such weight (such as the aforementioned categories in the strenuousness category type 404A-404E combined with radiation level 402D). In such cases, no weighting needs to be applied to the input from sensors of those input types.

It should also be noted that as described earlier it is possible for a single task to be assigned into two different categories of two different category types. For example, a particular task may be both strenuous and somewhat dangerous. Situations where multiple categories in multiple category types can be assigned to the same task may be handled in a variety of ways. In a first example embodiment, the table 400 in FIG. 4 could be utilized. As can be seen, however, it would then be possible for two different weights to be assigned to the same input sensor type, if both category types have a designated weight in the chart for the same input sensor type. This potential conflict could be resolved by, for example, selecting one of the possible weights (perhaps the highest weight). Alternatively, each category type can be ranked so that there is a priority of category types, and the weight corresponding to the highest ranked category type may be utilized (e.g., dangerousness may be considered more important than strenuousness). Another possibility is to average the multiple possible weights. Yet another possibility is to multiply the multiple possible weights, thus possibly amplifying their affects).

In another example embodiment, a different table or alternative data structure may be used that can track the various combinations of different category types and sensor input types and assign a single weight to each combination. For example, a three dimensional data structure can be constructed with strenuousness on one axis, dangerousness on another axis, and sensor input type on another axis, with the values in the data structures being the weights assigned to the various combinations.

While the table showing sensor weights for various combinations of task categories and sensors may be used as a basis to establish the weights for particular sensor data, in an example embodiment additional variables also affect these weights. For example, the accuracy of a sensor may also be used to modify the weight of data from the sensor.

Referring back to FIG. 3, at operation 312, a current safety score may be calculated for the worker. This current safety score may be based on the calculation of a formula, with the formula using the assigned weights as coefficients to variables for the data values from various sensors. In a simple example, the formula may be represented as follows:

$$S=a_1x_1+a_2x_2+\ldots+a_nx_n$$

where $x_n$ is the data from sensor n and $a_n$ is the weight assigned to sensor n.

At operation 314, the current safety score is compared to a safety threshold. As with the weights, the safety threshold may, in some example embodiments, vary based on the task currently being performed and/or the category or categories of such a task. In other example embodiments, the safety threshold may vary based on other information, such as overall worker health condition or previous safety violations. For example, if the worker has recently returned from a medical leave for a heart attack, the safety threshold may be lowered for that worker so as to trigger a safety alert in situations where other workers may not have an alert generated.

At operation 316, in response to a determination that the current safety score violates the safety threshold, an alert is generated to the worker indicating that the worker is in danger. In some example embodiments, these alerts may be generated to one or more devices on the person of the worker, such as smart safety glasses 118A, a smart helmet 118B, and a wearable computer 118C of FIG. 1. At operation 318, alerts are generated to other entities identified in the CIS information (such as the worker's supervisor, or medical personnel).

Figure 5:
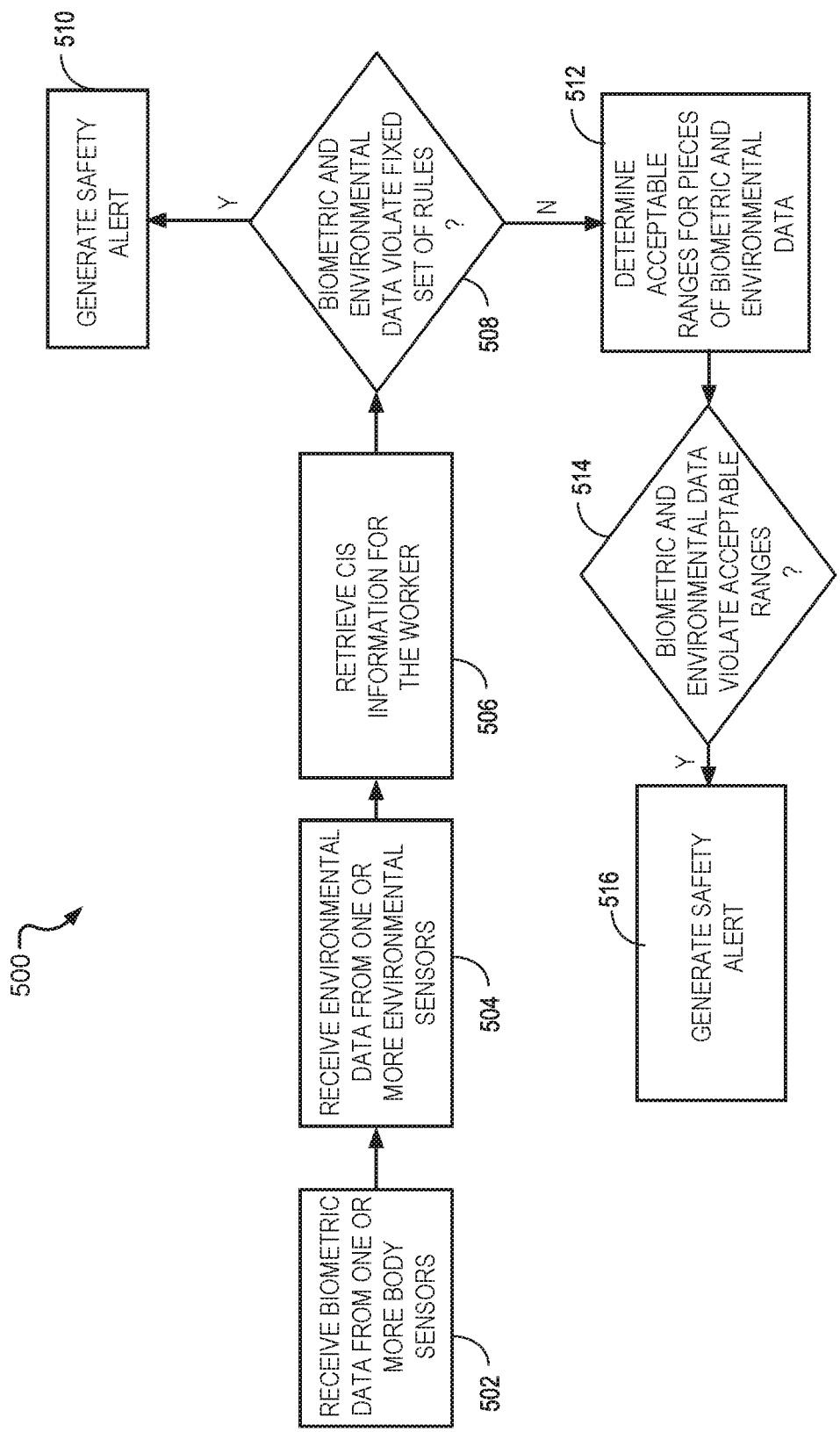
FIG. 5 is a flow diagram illustrating a method, in accordance with an example embodiment, of generating safety alerts.

FIG. 5 is a flow diagram illustrating a method 500, in accordance with an example embodiment, of generating safety alerts. At operation 502, biometric data is received from one or more body sensors monitoring a worker. At operation 504, environmental data is received from one or more environmental sensors in an area surrounding the worker. At operation 506, CIS information is retrieved for the worker. The CIS information can include context information for the worker (for example, current assignment, task, location, task intensity, known issues, etc.).

At operation 508, the biometric data and environmental data are compared against a fixed set of rules. This fixed set of rules may be a nominal set including rules that should generate a safety alert regardless of the current context. Examples of such rules may include a heart rate that exceeds a rate that is safe for anyone (e.g., heart rate about 180 bpm), temperature above a particular degree (e.g., above 102 degrees Fahrenheit), and the like. The reasoning behind these fixed rules are that there are some critical situations that should be acted upon immediately, without taking the time to do deeper analysis.

Thus, at operation 510, if one or more rules of the fixed set of rules are triggered, then a safety alert is generated. If this occurs, then the process may end. If not, then at operation 512, an acceptable range for each of the pieces of biometric and environmental data is determined. This acceptable range is based on the current context, and thus the range will differ based on different contexts. Thus, for example, if the context includes a location that is currently experiencing high temperatures in general (e.g., outside in Phoenix, Ariz. in the summer), the acceptable range for body temperature may be higher than in normal temperature conditions (and, similarly, a lower range of acceptable body temperatures may be used for winter in Minneapolis, Minn.).

Figure 6:
FIG. 6 is an example of a table assigning acceptable ranges to various combinations of context and sensor input types, in accordance with an example embodiment.

FIG. 6 is an example of a table 600 assigning acceptable ranges to various combinations of context and sensor input types, in accordance with an example embodiment. It should be noted that this table 600 may be stored in a computer system or database as a three dimensional data structure, having location on one axis, season on a second axis, and sensor input type on a third axis. However, for simplicity, FIG. 6 depicts the table 600 as a two dimensional data structure having various combinations of contexts assigned to rows 602A-602H and sensor input types assigned to the columns 604A-604C.

The values assigned to the combinations of combinations of contexts 602A-602H and sensor input types 604A-604C are acceptable ranges for the corresponding sensor input types 604A-604C. For example, if the context is that the location is in Phoenix and the season is the summer 602C), and the sensor input type is temperature (604A), then the value 606 is the range of 97.0°-101°, whereas if the context is that the location is in Minneapolis, the season is winter 602E, and the sensor input type is heart rate, then the value 608 is the range of 60-140 bpm.

As the number of different potential measurable or determinable contexts rises, the complexity of the table 600 or corresponding underlying data structure may also rise. For example, there may be 10 different context types, in which case an 11-dimensional data structure may be used to store acceptable ranges for various combinations of contexts of various context types and sensor input types.

Referring back to FIG. 5, at operation 514, each piece of biometric and environmental data is compared against the determined respective acceptable ranges (based on context). If any of these ranges are violated, then a safety alert is generated at operation 516.

In a first example scenario, a field engineer is performing maintenance on a nuclear power plant and he is not very familiar with the area. He walks into a high-risk, restricted area. The system triggers a warning notifying him and his supervisor of the risk of radiation exposure. The engineer's location is determined by beacons installed in the power plant equipment, access to the area is determined by the employee clearance and assignment registered in the corporate system, and exposure to radiation is determined by smart sensors on his body. In this case, the various pieces of context information include the worker location, task currently assigned to the worker, and worker familiarity with the task or location (from the worker's personnel file). The system may utilize this context information to establish acceptable ranges or parameters for various sensor input types. Failure to comply with these parameters and excessive exposure to radiation will result in the generation of a security and safety alert. It should be noted that this illustrates an example of a case where location may be both a context and a sensor input type, and thus also illustrates a situation where both context and sensor input type information may be derived from the same sensor (e.g., a beacon, GPS receiver, RFID scanner, or the like). Additionally, an acceptable location for the user (based on the task currently assigned to the user) may also be considered a category of context utilized in such an example (or, at least, as a sub-category of the task currently assigned to the worker).

In another example scenario, an employee is on a factory floor working on a complex procedure that involves a risky task. The system is aware of the procedure and its tasks, based on inputs from the corporate information system. As the employee moves around on the factory floor, the system infers the current task based on proximity to equipment and tools, location on the factory floor determined by indoor location positioning infrastructure, and status updates from the employee. When a risky task is about to be undertaken, the system generates a warning reminding the user of procedures and equipment. If the equipment has sensors (e.g., RFID tags), the system can also determine if the equipment is not being worn (for example, if the safety glasses or the safety helmet is not close to the employee). This would trigger a visual or audible alert to the worker and potentially to his supervisors.

Example Mobile Device

Figure 7:
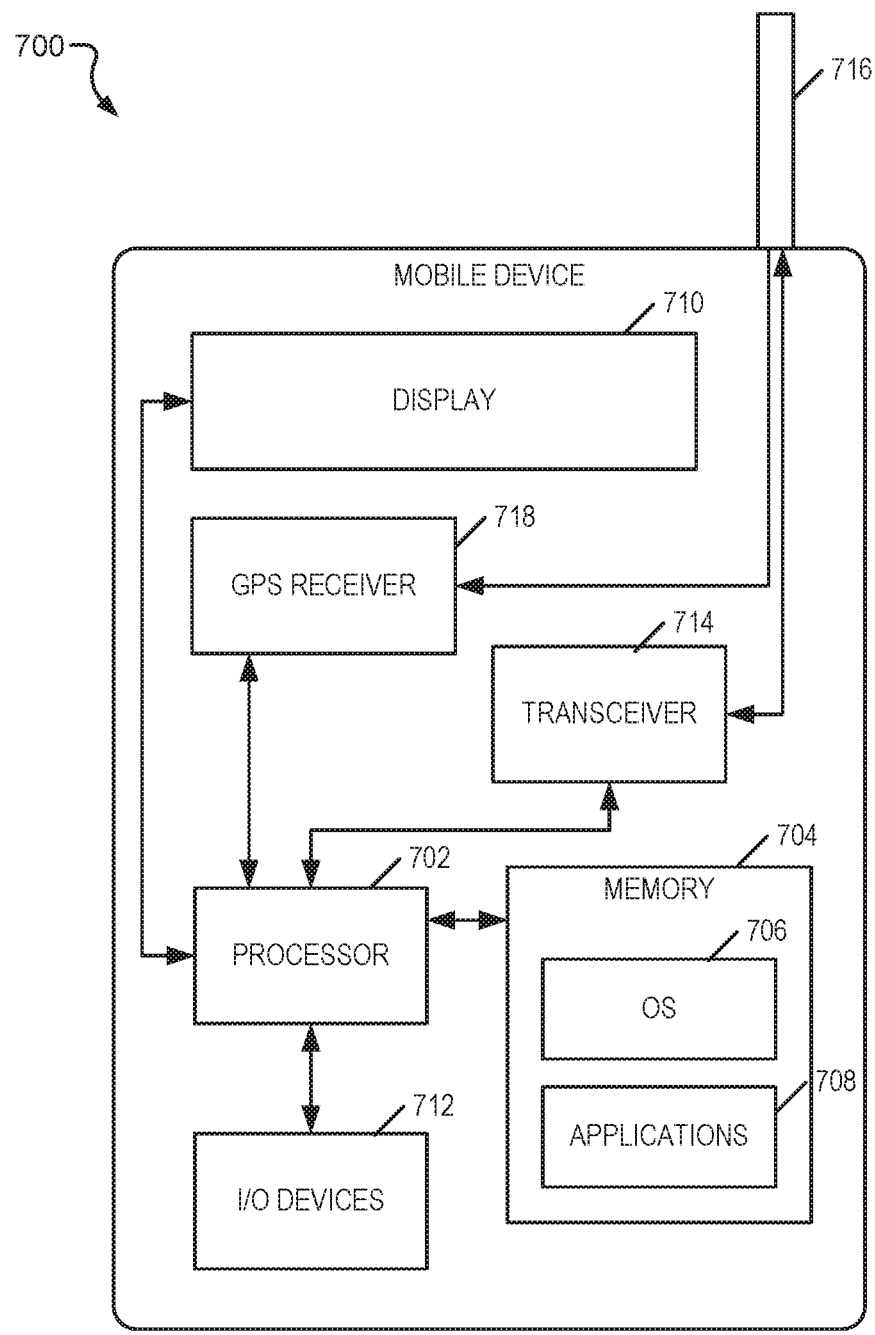
FIG. 7 is a block diagram illustrating a mobile device, according to an example embodiment.

FIG. 7 is a block diagram illustrating a mobile device 700, according to an example embodiment. The mobile device 700 can include a processor 702. The processor 702 can be any of a variety of different types of commercially available processors suitable for mobile devices 700 (for example, an XScale architecture microprocessor, a Microprocessor without interlocked Pipeline Stages (MIPS) architecture processor, or another type of processor). A memory 704, such as a random access memory (RAM), a Flash memory, or another type of memory, is typically accessible to the processor 702. The memory 704 can be adapted to store an operating system (OS) 706, as well as applications 708, such as a mobile location enabled application that can provide location based services (LBSs) to a user. The processor 702 can be coupled, either directly or via appropriate intermediary hardware, to a display 710 and to one or more input/output (I/O) devices 712, such as a keypad, a touch panel sensor, a microphone, and the like. Similarly, in some embodiments, the processor 702 can be coupled to a transceiver 714 that interfaces with an antenna 716. The transceiver 714 can be configured to both transmit and receive cellular network signals, wireless data signals, or other types of signals via the antenna 716, depending on the nature of the mobile device 700. Further, in some configurations, a GPS receiver 718 can also make use of the antenna 716 to receive GPS signals.

Modules, Components and Logic

Certain embodiments are described herein as including logic or a number of components, modules, or mechanisms. Modules can constitute either software modules (e.g., code embodied (1) on a non-transitory machine-readable medium or (2) in a transmission signal) or hardware-implemented modules. A hardware-implemented module is a tangible unit capable of performing certain operations and can be configured or arranged in a certain manner. In example embodiments, one or more computer systems (e.g., a standalone, client, or server computer system) or one or more processors can be configured by software (e.g., an application or application portion) as a hardware-implemented module that operates to perform certain operations as described herein.

In various embodiments, a hardware-implemented module can be implemented mechanically or electronically. For example, a hardware-implemented module can comprise dedicated circuitry or logic that is permanently configured (e.g., as a special-purpose processor, such as afield programmable gate array (FPGA) or an application-specific integrated circuit (ASIC)) to perform certain operations. A hardware-implemented module can also comprise programmable logic or circuitry (e.g., as encompassed within a general-purpose processor or other programmable processor) that is temporarily configured by software to perform certain operations. It will be appreciated that the decision to implement a hardware-implemented module mechanically, in dedicated and permanently configured circuitry, or in temporarily configured circuitry (e.g., configured by software) can be driven by cost and time considerations.

Accordingly, the term "hardware-implemented module" should be understood to encompass a tangible entity, be that an entity that is physically constructed, permanently configured (e.g., hardwired), or temporarily or transitorily configured (e.g., programmed) to operate in a certain manner and/or to perform certain operations described herein. Considering embodiments in which hardware-implemented modules are temporarily configured (e.g., programmed), each of the hardware-implemented modules need not be configured or instantiated at any one instance in time. For example, where the hardware-implemented modules comprise a general-purpose processor configured using software, the general-purpose processor can be configured as respective different hardware-implemented modules at different times. Software can accordingly configure a processor, for example, to constitute a particular hardware-implemented module at one instance of time and to constitute a different hardware-implemented module at a different instance of time.

Hardware-implemented modules can provide information to, and receive information from, other hardware-implemented modules. Accordingly, the described hardware-implemented modules can be regarded as being communicatively coupled. Where multiple such hardware-implemented modules exist contemporaneously, communications can be achieved through signal transmission (e.g., over appropriate circuits and buses that connect the hardware-implemented modules). In embodiments in which multiple hardware-implemented modules are configured or instantiated at different times, communications between such hardware-implemented modules can be achieved, for example, through the storage and retrieval of information in memory structures to which the multiple hardware-implemented modules have access. For example, one hardware-implemented module can perform an operation and store the output of that operation in a memory device to which it is communicatively coupled. A further hardware-implemented module can then, at a later time, access the memory device to retrieve and process the stored output. Hardware-implemented modules can also initiate communications with input or output devices, and can operate on a resource (e.g., a collection of information).

The various operations of example methods described herein can be performed, at least partially, by one or more processors that are temporarily configured (e.g., by software) or permanently configured to perform the relevant operations. Whether temporarily or permanently configured, such processors can constitute processor-implemented modules that operate to perform one or more operations or functions. The modules referred to herein can, in some example embodiments, comprise processor-implemented modules.

Similarly, the methods described herein can be at least partially processor-implemented. For example, at least some of the operations of a method can be performed by one of processors or processor-implemented modules. The performance of certain of the operations can be distributed among the one or more processors, not only residing within a single machine, but deployed across a number of machines. In some example embodiments, the processor or processors can be located in a single location (e.g., within a home environment, an office environment, or a server farm), while in other embodiments the processors can be distributed across a number of locations.

The one or more processors can also operate to support performance of the relevant operations in a "cloud computing" environment or as a "software as a service" (SaaS). For example, at least some of the operations can be performed by a group of computers (as examples of machines including processors), these operations being accessible via a network (e.g., the Internet) and via one or more appropriate interfaces (e.g., application program interfaces (APIs)).

Electronic Apparatus and System

Example embodiments can be implemented in digital electronic circuitry, in computer hardware, firmware, or software, or in combinations of them. Example embodiments can be implemented using a computer program product, e.g., a computer program tangibly embodied in an information carrier, e.g., in a machine-readable medium for execution by, or to control the operation of data processing apparatus, e.g., a programmable processor, a computer, or multiple computers.

A computer program can be written in any form of description language, including compiled or interpreted languages, and it can be deployed in any form, including as a standalone program or as a module, subroutine, or other unit suitable for use in a computing environment. A computer program can be deployed to be executed on one computer or on multiple computers at one site or distributed across multiple sites and interconnected by a communication network.

In example embodiments, operations can be performed by one or more programmable processors executing a computer program to perform functions by operating on input data and generating output. Method operations can also be performed by, and apparatus of example embodiments can be implemented as, special purpose logic circuitry, e.g., an FPGA or an ASIC.

The computing system can include clients and servers. A client and server are generally remote from each other and typically interact through a communication network. The relationship of client and server arises by virtue of computer programs running on the respective computers and having a client-server relationship to each other. In embodiments deploying a programmable computing system, it will be appreciated that both hardware and software architectures merit consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware can be a design choice. Below are set out hardware (e.g., machine) and software architectures that can be deployed, in various example embodiments.

Example Machine Architecture and Machine-Readable Medium

Figure 8:
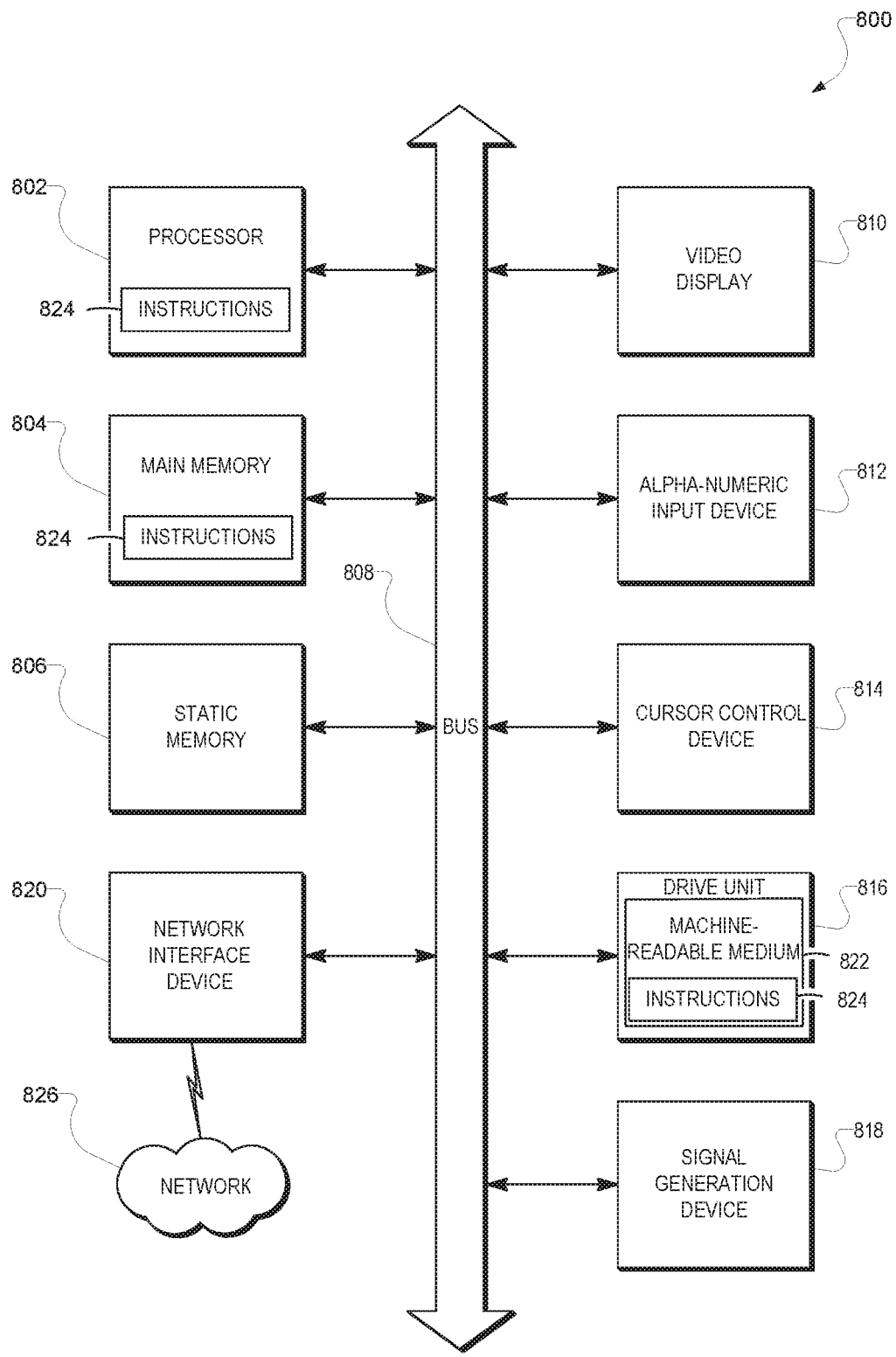
FIG. 8 is a block diagram of a machine in the example form of a computer system within which instructions may be executed to cause the machine to perform any one or more of the methodologies discussed herein.

FIG. 8 is a block diagram of a machine in the example form of a computer system 800 within which instructions 824 may be executed to cause the machine to perform any one or more of the methodologies discussed herein. In alternative embodiments, the machine operates as a standalone device or can be connected (e.g., networked) to other machines. In a networked deployment, the machine can operate in the capacity of a server or a client machine in server-client network environment, or as a peer machine in a peer-to-peer (or distributed) network environment. The machine can be a personal computer (PC), a tablet PC, a set-top box (SIB), a personal digital assistant (PDA), a cellular telephone, a web appliance, a network router, switch, or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 800 includes a processor 802 (e.g., a central processing unit (CPU), a graphics processing unit (GPU), or both), a main memory 804, and a static memory 806, which communicate with each other via a bus 808. The computer system 800 can further include a video display 810 (e.g., a liquid crystal display (LCD) or a cathode ray tube (CRT)). The computer system 800 also includes an alphanumeric input device 812 (e.g., a keyboard or a touch-sensitive display screen), a user interface (UI) navigation (or cursor control) device 814 (e.g., a mouse), a disk drive unit 816, a signal generation device 818 (e.g., a speaker), and a network interface device 820.

Machine-Readable Medium

The disk drive unit 816 includes a machine-readable medium 822 on which are stored one or more sets of data structures and instructions 824 (e.g., software) embodying or utilized by any one or more of the methodologies or functions described herein. The instructions 824 can also reside, completely or at least partially, within the main memory 804 and/or within the processor 802 during execution thereof by the computer system 800, with the main memory 804 and the processor 802 also constituting machine-readable media 822.

While the machine-readable medium 822 is shown in an example embodiment to be a single medium, the term "machine-readable medium" can include a single medium or multiple media (e.g., a centralized or distributed database, and/or associated caches and servers) that store the one or more instructions 824 or data structures. The term "machine-readable medium" shall also taken to include any tangible medium that is capable of storing, encoding, or carrying instructions 824 for execution by the machine and that cause the machine to perform any one or more of the methodologies of the present disclosure, or that is capable of storing, encoding, or carrying data structures utilized by or associated with such instructions 824. The term "machine-readable medium" shall accordingly be taken to include, but not be limited to, solid-state memories, and optical and magnetic media. Specific examples of machine-readable media 822 include non-volatile memory, including by way of example semiconductor memory devices, e.g., erasable programmable read-only memory (EPROM), electrically erasable programmable read-only memory (EEPROM), and flash memory devices; magnetic disks such as internal hard disks and removable disks; magneto-optical disks; and CD-ROM and DVD-ROM disks.

Transmission Medium

The instructions 824 can be transmitted or received over a communication network 826 using a transmission medium. The instructions 824 can be transmitted using the network interface device 820 and any one of a number of well-known transfer protocols (e.g., HTTP). Examples of communication networks include a local area network (LAN), a wide area network (WAN), the Internet, mobile telephone networks, plain old telephone (POTS) networks, and wireless data networks (e.g., WiFi and WiMax networks). The term "transmission medium" shall be taken to include any intangible medium that is capable of storing, encoding, or carrying instructions 824 for execution by the machine, and includes digital or analog communications signals or other intangible media to facilitate communication of such software.

Although an embodiment has been described with reference to specific example embodiments, it will be evident that various modifications and changes can be made to these embodiments without departing from the broader spirit and scope of the disclosure. Accordingly, the specification and drawings are to be regarded in an illustrative rather than a restrictive sense. The accompanying drawings that form a part hereof show by way of illustration, and not of limitation, specific embodiments in which the subject matter can be practiced. The embodiments illustrated are described in sufficient detail to enable those skilled in the art to practice the teachings disclosed herein. Other embodiments can be utilized and derived therefrom, such that structural and logical substitutions and changes can be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter can be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose can be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

This written description uses examples to disclose the inventive subject matter, including the best mode, and also to enable any person skilled in the art to practice the inventive subject matter, including making and using any devices or systems and performing any incorporated methods. The patentable scope of the inventive subject matter is defined by the claims and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A method comprising:
   receiving, at a rules engine executable by one or more processors, biometric data from one or more body sensors monitoring a user;
   receiving, at the rules engine, environmental data from one or more environmental sensors in an area surrounding the user;
   retrieving, from a server, activity information associated with the user;
   determining, at the rules engine, an activity being performed by the user based on the activity information;
   assigning, at the rules engine, weights to the biometric data and the environmental data, the weights assigned to the biometric data being different than the weight assigned to the environmental data, the weights assigned based on the task currently being performed by the user;
   calculating, at the rules engine, a current safety score for the worker using the assigned weights as coefficients to variables, the variables being values obtained from the biometric data and the environmental data;
   comparing, at the rules engine, the current safety score with a reference safety score; and
   based on the comparing, generating, at the rules engine, a safety indicator.

2. The method of claim 1, wherein the safety value is a safety threshold, and the safety indicator is an alert to indicate that the safety threshold has been reached.

3. The method of claim 1, further comprising:
   wirelessly sending the safety indicator to smart glasses worn by the user.

4. The method of claim 1, further comprising:
   wirelessly sending the safety indicator to a wearable computer worn by the user.

5. The method of claim 1, wherein the activity information includes user health information; and
   wherein the weights are further based on the user health information, thus personalizing the weights for individual user health conditions.

6. The method of claim 1, wherein the environmental data includes information from a Radio Frequency ID (RFID) scanner on a machine, the environmental data identifying a tool having an embedded RFID chip that has been passed next to the RFID scanner, the method further comprising verifying that the worker is performing the task via the information from the RFID scanner.

7. The method of claim 1, wherein the assigned weights are stored in a multidimensional data structure in a database, the multidimensional data structure having a plurality of axes each corresponding to a different task category type and an axis corresponding to body and environmental sensor type, with values stored in the multidimensional data structure corresponding to the assigned weights.

8. A system comprising:
   a server containing activity information for the user;
   a rules engine executable by one or more processors and configured to:
   receive, at a rules engine executable by one or more processors, biometric data from one or more body sensors operatively monitoring a user;
   receive, at the rules engine, environmental data from one or more environmental sensors in an area operatively surrounding the user;
   retrieve, from a server, activity information associated with the user;
   determine, at the rules engine, an activity being performed by the user based on the activity information;
   assign, at the rules engine, weights to the biometric data and the environmental data, the weights assigned to the biometric data being different than the weight assigned to the environmental data, the weights assigned based on the task operatively being performed by the user;
   calculate, at the rules engine, a current safety score for the worker using the assigned weights as coefficients to variables, the variables being values obtained from the biometric data and the environmental data;
   compare, at the rules engine, the current safety score with a reference safety score; and
   based on the comparing, generate, at the rules engine, a safety indicator.

9. The system of claim 8, wherein the safety value is a safety threshold, and the safety indicator is an alert to indicate that the safety threshold has been reached.

10. The system of claim 8, the rules engine further configured to:
    wirelessly send the alert to smart glasses worn by the worker.

11. The system of claim 8, the rules engine further configured to:

wirelessly send the alert to a wearable computer worn by the user.

12. The system of claim 8, wherein the activity information includes user health information; and wherein the weights are further based on the user health information, thus personalizing the weights for individual user health conditions.

13. The system of claim 8, wherein the environmental data includes information from a Radio Frequency ID (RFID) scanner on a machine, the environmental data identifying a tool having an embedded RFID chip that has been passed next to the RFID scanner, the rules engine further configured to verify that the worker is performing the task via the information from the RFID scanner.

14. The system of claim 8, wherein the assigned weights are stored in a multidimensional data structure in a database, the multidimensional data structure having a plurality of axes each corresponding to a different task category type and an axis corresponding to body and environmental sensor type, with values stored in the multidimensional data structure corresponding to the assigned weights.

15. A non-transitory machine-readable storage medium comprising instructions, which when implemented by one or more machines, cause the one or more machines to perform operations, the operations comprising:

receiving biometric data from one or more body sensors monitoring a worker;

receiving, at a rules engine executable by one or more processors, biometric data from one or more body sensors monitoring a user;

receiving, at the rules engine, environmental data from one or more environmental sensors in an area surrounding the user;

retrieving, from a server, activity information associated with the user;

determining, at the rules engine, an activity being performed by the user based on the activity information;

assigning; at the rules engine, weights to the biometric data and the environmental data, the weights assigned to the biometric data being different than the weight assigned to the environmental data, the weights assigned based on the task currently being performed by the user;

calculating, at the rules engine, a current safety score for the worker using the assigned weights as coefficients to variables, the variables being values obtained from the biometric data and the environmental data;

comparing, at the rules engine, the current safety score with a reference safety score; and based on the comparing, generating, at the rules engine, a safety indicator.

16. The non-transitory machine-readable storage medium of claim 15, wherein the safety value is a safety threshold, and the safety indicator is an alert to indicate that the safety threshold has been reached.

17. The non-transitory machine-readable storage medium of claim 15, the operations further comprising:

wirelessly sending the alert to smart glasses worn by the worker.

18. The non-transitory machine-readable storage medium of claim 15, the operations further comprising:

wirelessly sending the alert to a wearable computer worn by the user.

19. The non-transitory machine-readable storage medium of claim 15, wherein the activity information includes user health information; and wherein the weights are further based on the user health information, thus personalizing the weights for individual user health conditions.

20. The non-transitory machine-readable storage medium of claim 15, wherein the assigned weights are stored in a multidimensional data structure in a database, the multidimensional data structure having a plurality of axes each corresponding to a different task category type and an axis corresponding to body and environmental sensor type, with values stored in the multidimensional data structure corresponding to the assigned weights.

\* \* \* \* \*

UNITED STATES PATENT AND TRADEMARK OFFICE
CERTIFICATE OF CORRECTION

PATENT NO. : 9,792,798 B2
APPLICATION NO. : 15/407187
DATED : October 17, 2017
INVENTOR(S) : Jobin et al.

It is certified that error appears in the above-identified patent and that said Letters Patent is hereby corrected as shown below:

In the Claims

In Column 15, Line 38, in Claim 15, delete "assigning;" and insert --assigning,-- therefor Signed and Sealed this
Twenty-eighth Day of May, 2019

Andrei Iancu
*Director of the United States Patent and Trademark Office*